US005410604A

United States Patent [19]

Saito et al.

[11] Patent Number: 5,410,604

[45] Date of Patent: Apr. 25, 1995

[54] SYSTEM FOR REDUCING NOISE SOUNDING IN PASSENGER COMPARTMENT OF VEHICLE

[75] Inventors: Hiroyuki Saito, Katsuta; Masahiro Kusano, Zama, both of Japan

[73] Assignee: Nissan Motor Co., Ltd., Yokohama, Japan

[21] Appl. No.: 867,827

[22] Filed: Apr. 14, 1992

[30] Foreign Application Priority Data

Apr. 16, 1991 [JP] Japan ................................ 3-083861

[51] Int. Cl.$^{6}$ ....................... A61F 11/06; H03B 29/00

[52] U.S. Cl. ................................................ 381/71

[58] Field of Search .................................. 381/71, 94

[56] References Cited

U.S. PATENT DOCUMENTS 4,596,033 6/1986 Swinbanks ........................... 381/71
4,656,993 4/1987 Yuzawa et al. .
4,677,676 6/1987 Eriksson ................................ 381/71
4,683,590 7/1987 Miyoshi et al. ........................ 381/71
4,747,389 5/1988 Yuzawa et al. .
5,022,082 6/1991 Eriksson et al. ...................... 381/71
5,029,218 7/1991 Nagayasu ............................. 381/71
5,170,433 12/1992 Elliott et al. .

FOREIGN PATENT DOCUMENTS 1341909 9/1991 Japan .
1341911 9/1991 Japan .
2149614 6/1985 United Kingdom .
PCT/GB87/-00706 10/1987 WIPO .

OTHER PUBLICATIONS

Elliott et al. publication, vol. ASSP-35, No. 10, Oct. 1987 entitled "A Multiple Error LMS algorithm and its Application to the Act of Control of Error LMS Algorithm and its Application to the Act of Control of Sount and Vibration".

*Primary Examiner*—Curtis Kuntz
*Assistant Examiner*—Ping W. Lee
*Attorney, Agent, or Firm*—Lowe, Price, LeBlanc & Becker

[57] ABSTRACT

A system for reducing a closed sound generated by propagation of vibrations into a limited space such as a vehicular compartment using at least one microphone and at least one speaker. In the closed sound reducing system, a volatile memory such as a RAM is installed for storing a measured newest value of a vibration propagation transfer function cfm(j) and a non-volatile memory such as a ROM is installed for storing a standard value of the vibration propagation transfer function. When the stored data of the volatile memory is erased, the standard value stored in the non-volatile memory is used in place of the measured newest value stored in the volatile memory.

18 Claims, 4 Drawing Sheets

SYSTEM FOR REDUCING NOISE SOUNDING IN PASSENGER COMPARTMENT OF VEHICLE

BACKGROUND OF THE INVENTION (1) Field of the Invention

The present invention relates generally to a system for reducing noise sounding in a closed space due to a propagation of a vibrating noise in the closed space from a vibration source of a power unit (such as a vehicular engine) mounted in the vehicle (hereinafter referred to as a closed sound). Particularly, the present invention relates to the apparatus and system for reducing the closed sound sounded in the closed space due to the propagation in the closed space from the vibrations of the power unit which is easy in adjustment during an initial power supply of the apparatus.

(2) Description of the Background Art

Noises on secondary harmonics of the engine revolution speed, i.e., frequency components of an ignition frequency of a vehicular engine are propagated in the vehicular compartment of the vehicle, an unpleasant feeling is given to a vehicular driver.

Therefore, at least one speaker is mounted in the vehicular compartment to output a sound having a 180° opposite (out of phase) to the closed noise so as to cancel the closed noise.

A U.S. patent application Ser. No. 07/629, 637 exemplifies a previously proposed active noise cancelling system.

A PCT international patent application international publication W088/02912 exemplifies a previously proposed closed sound cancelling system. In the case disclosed in the PCT international patent application, since, at first, a white noise is output in the vehicular compartment and is detected through the microphone so that a spatial acoustic transfer characteristic in the vehicular compartment including an electric/acoustic conversion characteristic (function) between the microphone and speaker is identified. A value of the spatial acoustic transfer characteristic is stored into a memory. Using the stored content values, a plurality of filter coefficients to provide the 180-degree opposite sound by means of a steepest descent method in an adaptive digital filter are adaptively changed to reduce the closed sound. A volatile memory such as RAM is always used to update the stored values as the memory storing the spatial accoustic transfer characteristic.

In a case where the closed noise in the limited space is reduced using the previously proposed noise cancelling system disclosed in the above-identified PCT international publication (under PCT Article 20), the identification of the values on the spatial acoustic transfer characteristic using again, the white noise needs to be carried out when the power supply to the volatile memory is turned off and the content of the memory is accordingly erased or destroyed. If this previously proposed noise cancelling system is applied to an automotive vehicle, the content of the memory is destroyed when a battery of the vehicle is disconnected to repair or replace the battery. This requires a new setting operation for the previously proposed noise cancelling system by a user. Consequently, the reduction of the noise cancelling system into practice to the automotive vehicle becomes difficult.

SUMMARY OF THE INVENTION

It is an object of the present invention to provide an apparatus for reducing the closed sound in a vehicular compartment which is convenient for a vehicle user and which requires no identifying operation by the user for a spatial acoustic transfer characteristic even when the contents of a volatile memory is destroyed, the volatile memory storing a newest value of the spatial acoustic transfer function (characteristic).

The above-described objects can be achieved by providing a system for reducing a closed sound in a limited space, comprising: a) first means for receiving the closed sound wave generated due to a propagation from a noise source into the limited space, transducing the closed sound to output an electrical signal according to the closed sound wave; b) second means responsive to the electrical signal from said first means for calculating a new sound wave having the same amplitude as the closed sound wave and having a phase 180° opposite to the closed sound on a basis of an acoustic transfer characteristic of the limited space; c) third means for measuring the acoustic transfer characteristic of the limited space; d) a volatile memory for storing the measured value of the acoustic transfer characteristic as its stored data; and e) a non-volatile memory for storing a standard value of the acoustic transfer characteristic as its stored data, said second means calculating the new sound wave on the basis of the standard value of the acoustic transfer characteristic derived from the non-volatile memory when the stored data in the volatile memory is erased.

The above-described objects can also be achieved by providing a system for reducing a vibration propagated into a vehicular compartment, comprising: a) first means for receiving a harmonic signal of a vehicular engine vibration and outputting a cancelling sound wave against the harmonic signal; b) second means for detecting a state of a vibrating space created by means of a combination of the engine vibration and first means; c) third means for adjusting an output signal from the first means using a vibration propagation transfer function from a position of the first means to that of the second means so as to reduce a vibration energy detected by the second means; d) a volatile memory for storing a measured newest vibration propagation transfer function; and e) a non-volatile memory for previoiusly storing a standard value of the vibration propagation transfer function.

DETAILED DESCRIPTION OF THE PREFERRED EMBODIMENT

Reference will hereinafter be made to the drawings in order to facilitate a better understanding of the present invention.

Figure 2:
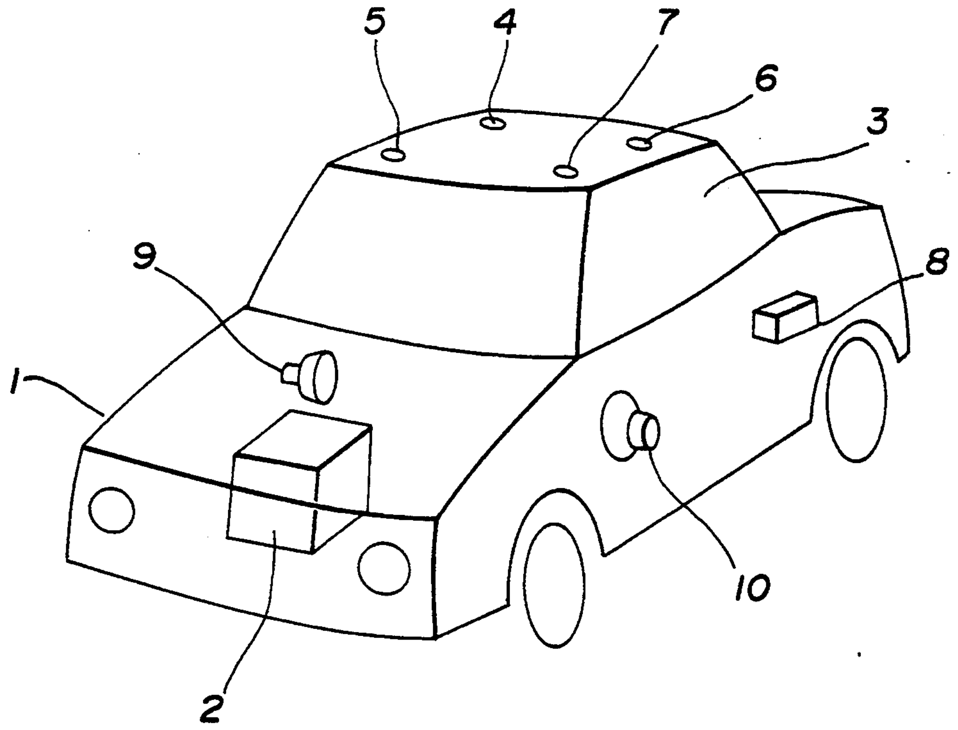
FIG. 2 is an overall external view of an automotive vehicle to which a closed sound reducing system according to the present invention is applicable.

FIG. 2 shows an external view of an automotive vehicle to which the present invention is applicable.

An internal combustion engine 2 is mounted on the vehicle 1, whose vibrations during its explosion strokes are propagated in a vehicular compartment via a vehicle body to form the closed sound.

The closed sound is detected by means of four microphones 4, 5, 6, and 7 attached on a ceiling portion of the vehicle body. The psuedo noise having the same amplitude as the closed noise and 180° opposite phase to the closed noise is calculated by means of a controller 8. The claculated psuedo noise is sounded from two speakers 9, 10 into the vehicular compartment 3. Thus, the closed sound is cancelled and reduced against the pseudo noise sound derived from the two speakers 9, 10.

Figure 3:
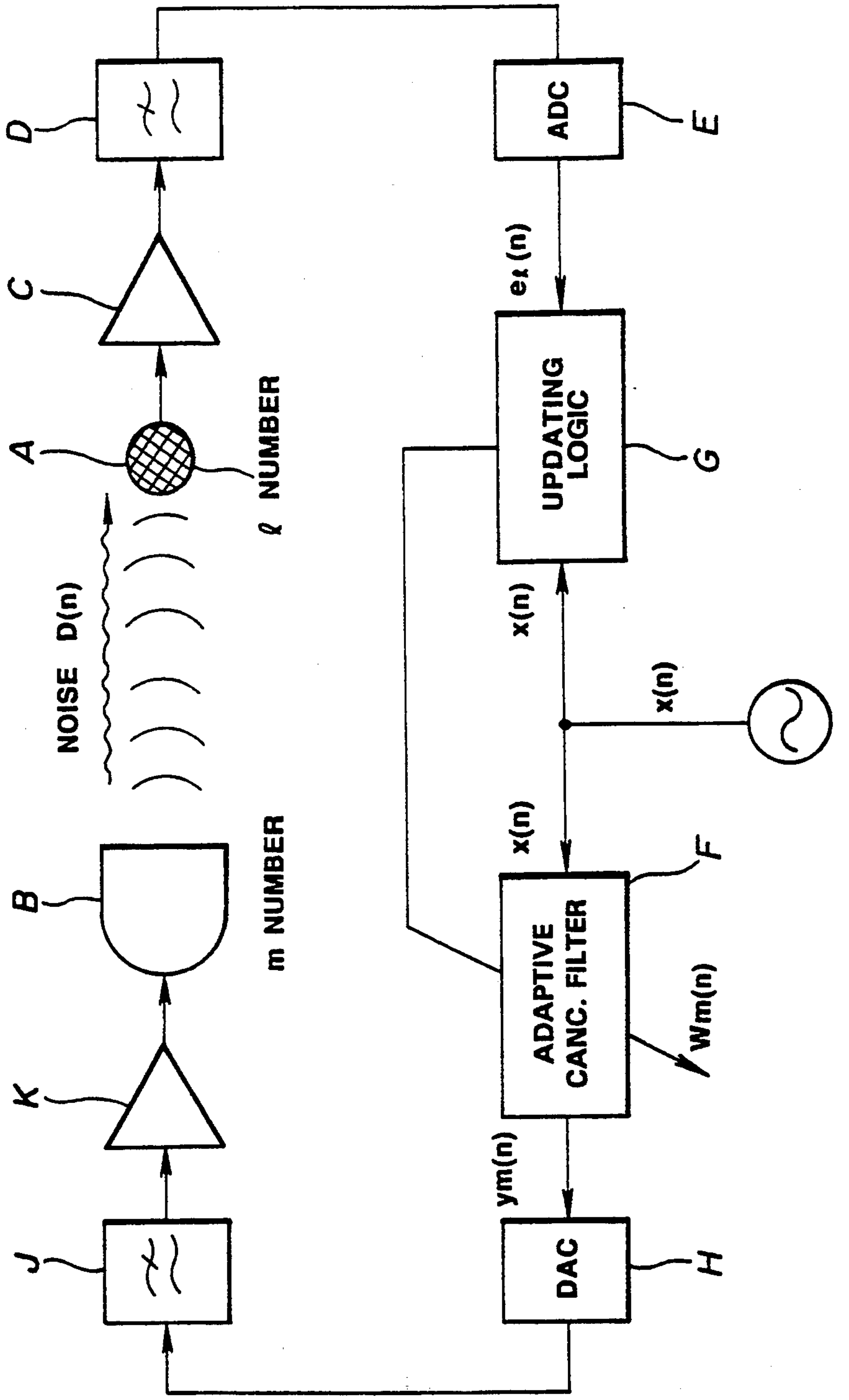
FIG. 3 is an explanatory view of a basic principle of a closed sound reduction to be carried out in the closed sound reducing system shown in FIG. 4.

FIG. 3 shows a .basic principle of reduction of the closed sound to facilitate understanding of the present invention.

It is noted that a U.S. patent application Ser. No. 07/629,637 exemplifies an operation of an adaptive cancelling filter as will be described later, the disclosure of which is herein incorporated by reference.

The system for reducing the closed noise in the preferred embodiment according to the present invention is called a multi-point noise reducing system constituted by an M number of speakers and L number of microphones.

The preferred embodiment shown in FIG. 2 is M=2, and L=4. Causes of the closed noise in the vehicle are based on ignition explosions of the engine. The period of the vibrations can be determined according to an ignition signal, a crank angle signal, and an engine revolution speed signal. U.S. Pat. No. 4,747,389 issued on May 31, 1988 and U.S. Pat. No. 4,656,998 issued on Apr. 14, 1987 exemplify a crank angle detector, the disclosures of which are herein incorporated by reference.

In the preferred embodiment, the engine revolution speed signal x(n) is a reference signal (n denotes a sampling period of time, n=p, 2, 3, - - - , T).

Sound input to the microphone A of number 1 of the L microphones serves as an interference sound of a noise Df(n) with an output sound from number m speaker B ($1 \leqq m \leqq M$).

The interference sound is converted into a digital signal by means of an analog/digital converter E via an amplifier C and a low-pass filter D. The digital signal output from the analog/digital converter E serves as a controlling input value (hereinafter, referred to as an error signal) ef(n).

On the other hand, the reference signal x (n) is input to the adaptive cancelling filter F whose output signal is indicated as the output $y_m(n)$ and is expressed in the following equation (1).

$$y_m(n) = \sum_{i=0}^{I-1} Wm(n, i) \times (n - i) \tag{1}$$

The adaptive filter described above is constituted by a Finite Impulse Response filter.

Coefficients Wm (n, i) of the adaptive filter are updated by means of, e.g., an LMS (Least Mean Square) algorithm as will be described later using the error signal ef(n) and reference signal x(n). The function of the adaptive filter is exemplified by a U.S. Pat. No. 5,029,118 issued on Jul. 2, 1991, the disclosure of which is herein incorporated by reference.

The output $y_m(n)$ from the adaptive filter F is converted into the analog signal via the digital/analog converter H. After amplified by an amplifier K through the low-pass filter J, the sound wave is output through the number m speaker B.

Suppose that the impulse response is cfm(j) ($0 \leqq j \leqq J-1$; J denotes the number of taps in the case of Impulse Response) (which corresponds to a spatial acoustic transfer function from the m number speaker in the frequency range to the f number microphone) in the time-discrete system from the sound wave received from the f number of microphone A and propagated from the space in the vehicular compartment The following equation (2) expresses the abovementioned cfm:

$$ef(n) = \sum_{m=1}^{M} \sum_{j=0}^{J-1} Cfm(j)\, y_m(n - j) + Df(n) \tag{2}$$

When the equation (1) is substituted into the equation (2), the following equation (3) is established:

$$ef(n) = \sum_{m=1}^{M} \sum_{j=0}^{J-1} cfm(j) \cdot \sum_{i=0}^{I-1} Wm(n - j, i) \times (n - j - i) + Df(n) \tag{3}$$

Suppose that Wm(n−j, i) is substantially equal to Wm(i) under a time invariant system. Then, the term ef(n) can be expressed in the following equation (4).

$$ef(n) = \sum_{m=1}^{M} \sum_{j=0}^{J-1} Wm(i) \cdot \sum_{j=0}^{J-1} Cfm(j) \times (n - j - i) + Df(n) \tag{4}$$

Suppose herein a function γflm (n) is defined as follows:

$$\sum_{j=0}^{J-1} Cfm(j) \times (n - j) \equiv \gamma fm(n) \tag{5}$$

then ef(n) can be expressed in the following equation (6).

$$ef(n) = \sum_{m=1}^{M} \sum_{i=0}^{I-1} Wm(i) fm(n - i) + Df(n) \tag{6}$$

The LMS algorithm described above is an algorithm which changes Wm(i) ($1 \leqq m \leqq M, 0 \leqq i \leqq I-1$) so as to minimize an evaluation function F expressed below:

$$F = \sum_{l=f}^{L} e^2 f(n)(n) \tag{7}$$

Specifically, the filter coefficients are updated using the following equation (8):

$$Wm(i) \leftarrow Wm(i) - A_2 \sum_{l=f}^{L}, \tag{8}$$

wherein $\alpha$ denotes the constant.

Figure 4:
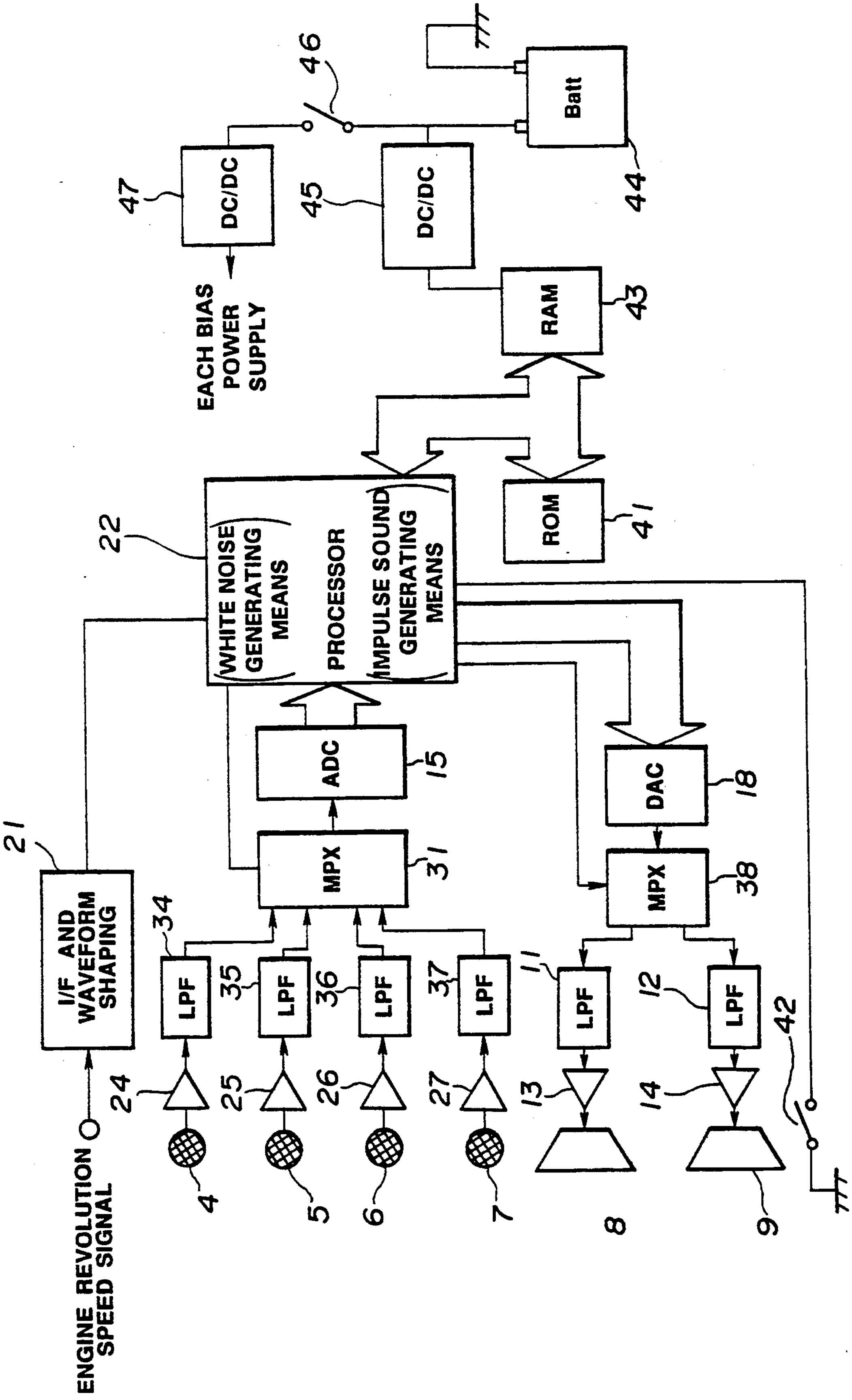
FIG. 4 is a structural explanatory view of the closed noise reducing system in the preferred embodiment.

FIG. 4 shows a specific structural view of the closed noise reducing system in the preferred embodiment.

The engine revolution speed signal is input into a circuit 21. The circuit 21 includes a comparator which serves as a waveform shaping and a level shifter which serves as a level compatible interface so that the engine revolution speed signal is converted into a processible signal for a microprocessor 22 (corresponds to the updating logic G of FIG. 3). It is noted that the processible signal is denoted by x(n) defined in the equation (1). The detection signals from the microphones 4 through 7 are passed through low-pass filters (filter D of FIG. 3) 34 through 37 constituted by amplifiers 24 through 27 (microphone C of FIG. 3) and active filter so as to be processed under an amplification and an anti-alias-filter processing. Thereafter, the detection signals of the microphones are input to the microprocessor 22 via the analog/digital converter 15 (converter E of FIG. 3). The output signals from the converter 15 to the processor 22 indicate signals ef(n) in the equation (8). (In the preferred embodiment, L=4).

The processor 22 updates Wm (i) in accordance with the equation (8). The output value $y_m$ is output in accordance with the equation (1). In the preferred embodiment, M=2.

The value $y_m$ is transmitted to a digit/analog converter 18 (converter H of FIG. 3) to be converted into the analog value, a multiplexer 38 switching output channels. The analog value of $y_m$ is thereafter passed through each low-pass filter 11, 12 (Filter J of FIG. 3) and amplifiers 13, 14 (amplifier K of FIG. 3) and is output via speakers 8, 9.

The output sound serves as a cancelling sound of the closed sound.

A program controlling the system whose structure is described above is stored in a ROM 41 (Read Only Memory) (which is a non-volatile memory) which is interconnected via a processor 22 and bus (this may be the ROM installed in an external of the system or may be installed in the internal processor). The reduction control of the closed sound in accordance with the read control program is carried out. The closed sound reduction control needs to identify the spatial acoustic transfer characteristic as described above. The values of identified acoustic transfer characteristics are once stored in the RAM 43 which is the volatile memory.

The stored values are used. The stored data of the RAM 43 are always backed up by means of a battery 44 via a DC/DC converter 45. In addition, a power of the battery 44 is supplied to other electrical equipment via an ignition switch 46 and DC/DC converter 47 of a different power supply line from a backup power of the RAM 43.

In addition, the switch 42 connected to the processor 22 is a switch operated to identify the acoustic transfer characteristic. A state of the switch 42 carries out the processing shown in details. In the preferred embodiment, standard values of the acoustic transfer characteristic in the RAM 43 are previously stored in the ROM 41 during a manufacturing shipment in order for the values of the acoustic transfer characteristics to be erased during replacement of the battery 44. As the standard values, the values cfm(j) of the same vehicle models are subjected to a fourier transform, average values of the amplitudes, and phase characteristics are derived and used.

In order to execute an LMS algorithm of the equation (8), the error signal ef(n) and values of cfm(j) and x(n) shown in the equation (5) are required.

ef(n) and x(n) denote the microphone input signal and the engine revolution speed signal as described before.

The signal cfm(j) corresponds to the spatial acoustic transfer function from the m number speaker to the f number microphone in the frequency region. Each speaker outputs a white noise or impulse sound, receiving the white noise or impulse sound through the microphone to identify the transfer function. The identifying processing carries out when the switch 42 is turned on.

Figure 1:
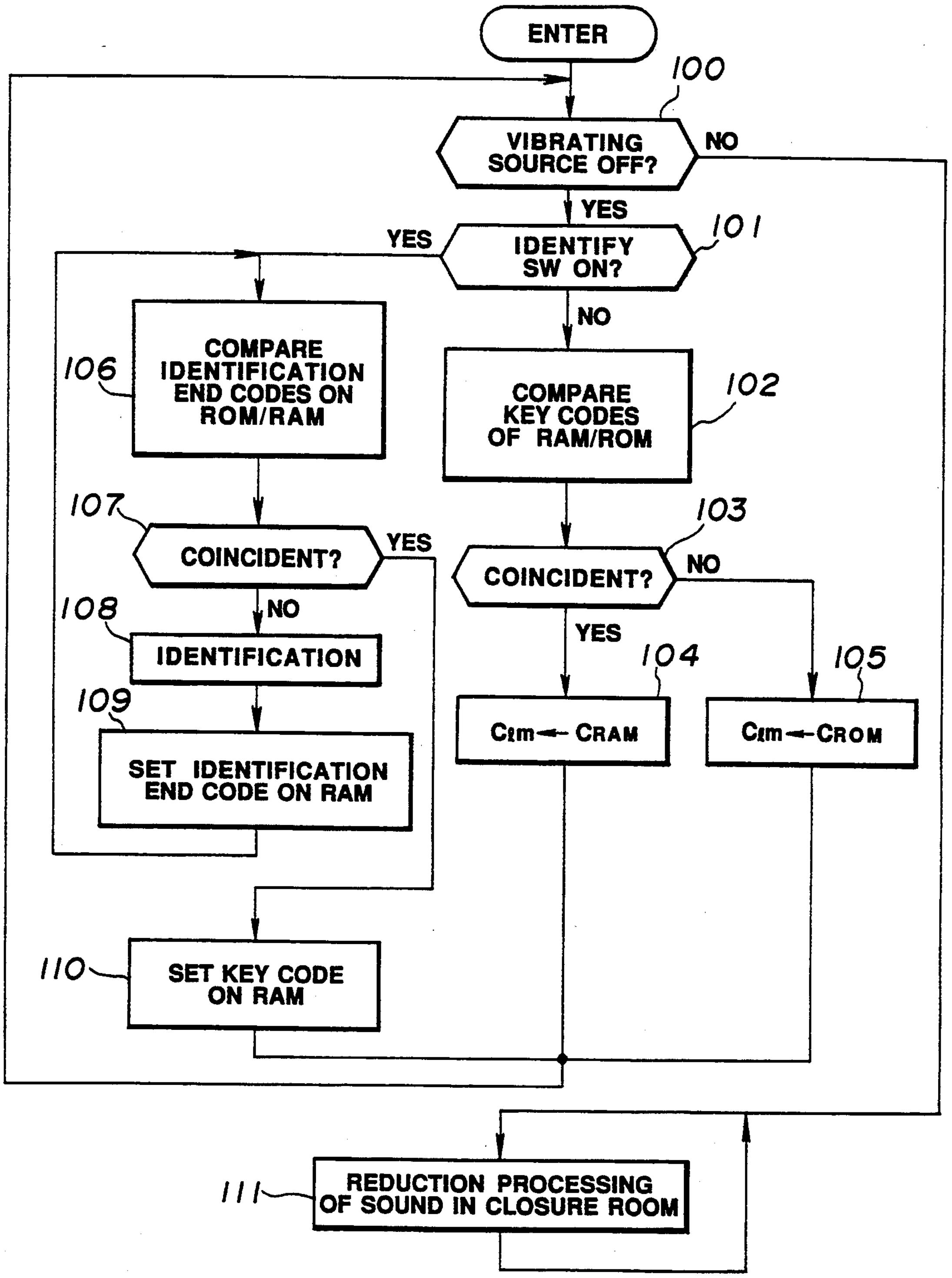
FIG. 1 is an operational flowchart of an identification processing procedure of a spatial acoustic transfer characteristic executed by a microprocessor of a closed sound reducing system in a preferred embodiment.

FIG. 1 shows the flowchart of the identification processing.

In a step 100 of FIG. 1, the microprocessor 22 determines whether the vibrating source, i.e., the engine is stopped. This determination is based on the determination whether, e.g., below a predetermined engine revolution speed (300 r.p.m.). If not stopped, the routine goes to a step 111 in which the normal closed noise reduction processing.

When the microprocessor 22 determines that the engine is stopped, the routine goes to a step 101.

In the step 101, the microprocessor 22 determines whether an identifying switch 42 is turned on or off. When determining that the identifying switch 42 is turned on in the step 101, the routine goes to a step 106 to compare an identification end code (as will be described below) in the ROM 41 and identification end code in the RAM 43.

When the result of comparison indicates coincidence in the next step 107, the processor 22 determines that the values of cfm(j) stored in the RAM 43 are values of correct newest acoustic transfer characteristic derived upon completion of the identification processing and the routine jumps to a step 110.

In the step 110, the microprocessor 22 sets a key code indicating that the data in the RAM 43 is correct data in the RAM 43 and the routine returns to a step 100.

When no coincidence determination of the result of comparison occurs in the step 107, the routine goes to a step 108 since it is certain that no identification is carried out.

The identification processing may include the method in which the white noise is output or alternatively the method in which the impulse sound is output.

After the identification end, the routine goes to a step 109 in which the identification end code is set (copied) in the RAM 43 to indicate that the identification processing is ended and the routine returns to a step 106.

In the step 101 if, the microprocessor 22 determines that the identifying switch 42 is turned off the routine goes to the step 107 in which the key code set in the RAM is compared with the key code in the ROM.

When the result of comparison indicates coincidence in a step 103, the value stored in the RAM 43 is used as the value cfm(j) in the calculation of the equation (8) (step 104).

When the result of comparison indicates no coincidence in the step 103, the routine goes to a step 105 in which the calculation of the equation (8) is carried out using the standard values in the ROM 41.

The reason of such use of the standard values in the ROM is that the data stored in the ROM are compensatedly used without execution of identification processing when the data in the RAM becomes volatile. When the user feels that the effect of the closed noise reduction is insufficient using the standard values, the identification switch 42 is turned on and the routine goes to the processing of the step 108 and values based on the accurate measurements are set in the RAM 43.

Although, in the preferred embodiment, the microphones and speakers are used to reduce the closed noise in the vehicular compartment, the present invention is applicable to a system for reducing the periodic noise reduction in a limited space or a system in which a vibration sensor installed on a vehicular floor and an engine mounted anti-vibration actuator are combined.

As described hereinabove, since data required to reduce the vibration or noise reduction can automatically be calculated using the data even if the data in the volatile memory are erased, the user can relieve the troublesome operation and convenience for handling the system can be improved.

It will fully be appreciated by those skilled in the art that the foregoing description has been made to the preferred embodiments and various changes and modifications may be made without departing from the scope of the present invention which is to be defined by the appended claims.

What is claimed is:

1. A system for reducing a sound in a limited space, comprising:

a) first means for receiving a sound wave generated due to a propagation from a noise source into the limited space, said noise source comprising a vehicular engine, and for transducing the sound wave to output an electrical signal according to the sound wave;

b) second means responsive to the electrical signal from said first means for calculating a new sound wave having the same amplitude as the sound wave and having a phase 180° opposite to the sound wave on a basis of a spatial acoustic transfer characteristic of the limited space for propagation of the new sound wave, said new sound wave being interfered with the sound wave propagated from the noise source;

c) third means for measuring the spatial acoustic transfer characteristic of the limited space;

d) a volatile memory for storing the measured value of the spatial acoustic transfer characteristic as its stored data;

e) a non-volatile memory for storing a standard value of the spatial acoustic transfer characteristic as its stored data, said second means calculating the new sound wave on the basis of the standard value of the spatial acoustic transfer characteristic derived from the non-volatile memory in place of the measured value of the spatial acoustic transfer characteristic from the volatile memory when the stored data in the volatile memory is erased, and an identifying switch, wherein said second means includes a microprocessor, wherein said microprocessor determines whether the engine is stopped and determines whether the identifying switch is turned on or off upon determining that the engine has stopped, and, when determining that the identifying switch is turned on, said microprocessor compares an identification end code in the volatile memory with an identification end code in the non-volatile memory, determines that the measured value of the spatial acoustic transfer characteristic stored in the volatile memory is a correct value of a newest acoustic transfer characteristic derived upon a previous identification processing when the identification end codes coincide with each other, sets a key code indicating that the data in the volatile memory is correct, and executes the identification processing when the identification end codes do not coincide with each other until the identification end codes coincide with each other.

2. A system for reducing a sound in a limited space as set forth in claim 1, wherein the limited space is a vehicular compartment.

3. A system for reducing a sound in a limited space as set forth in claim 2, wherein said volatile memory is a RAM and said non-volatile memory is a ROM.

4. A system for reducing a sound in a limited space as set forth in claim 3, wherein a power supply to said RAM is backed up by a vehicular battery and the standard value stored in said ROM is used to calculate the new sound wave in place of the measured value stored in the RAM when no back up power supply to the RAM occurs so that the measured value in the RAM is erased.

5. A system for reducing a sound in a limited space as set forth in claim 4, wherein the standard value stored in the ROM is a specified value determined for each vehicular model and stored during a shipment of the system.

6. A system for reducing a sound in a limited space as set forth in claim 5, wherein a bias supply of the RAM includes a DC/DC converter connected directly to the vehicular battery and the bias supply of another electrical equipment of the vehicle is connected to another DC/DC converter, said another DC/DC converter being connected to the vehicular battery via an ignition switch.

7. A system for reducing a sound in a limited space as set forth in claim 6, wherein said first means includes: an engine revolution speed sensor for detecting an engine revolution speed and outputting the engine revolution signal indicating the engine revolution speed; first signal processing means for shaping the engine revolution signal into a digital reference signal x(n) with a predetermined sampling period, where n is an integer representing a sample of the reference signal at an nth sampling period; a plurality of microphones installed on a ceiling portion of the vehicular compartment for receiving and transducing a combined sound wave resulting from the interference between the new sound wave and the sound wave propagated from the noise source in the vehicular compartment; a plurality of amplifiers and subsequent low-pass filters for amplifying the transduced sound wave signal from the respective microphones and subjecting the amplified and transduced sound wave signal to an anti-alias-filtering; and a multiplexer and A/D converter for converting the signal passed through the low-pass filters into a corresponding digital signal ell(n), and said second means is responsive to said digital reference signal x(n) and to said corresponding digital signal ell(n) for calculating said new sound wave.

8. A system for reducing a sound in a limited space as set forth in claim 7, wherein said second means further includes: a D/A converter connected to the microprocessor, a multiplexer connected to an output of the D/A converter, and a plurality of speakers respectively connected to the multiplexer and installed in the vehicular compartment for outputting the new sound wave.

9. A system for reducing a sound in a limited space as set forth in claim 8, wherein said microprocessor includes an adaptive filter of a Finite Impulse Response type having updated filter coefficients Wm (n, i) (wherein m=1 through M indicates the number of the speakers and i=0 through I−1 denotes the number of microphones) and the filter coefficients Wm(i) of the adaptive filter are updated by the microprocessor as follows:

$$Wm(i) \leftarrow Wm(i) - \alpha \sum_{l=1}^{L} el(n)\gamma lm(n-i),$$

wherein α denotes a constant and γlm(n−i) is expressed as follows:

$$\gamma lm(n) \equiv \sum_{j=0}^{J-1} Clm(j) \times (n-j),$$

wherein x(n−j) denotes a reference signal of j-th number of x(n), clm(j) (0≦j≦J−1; J denoting a number of taps in the Finite Impulse Response filter) denotes a system impulse response from a time when any one of the microphones receives the closed sound wave to a time when an error signal el(n) is output from the A/D converter and corresponds to an acoustic transfer function from an m-th number of the speakers to an l-th number of the microphones, the value of Clm(j) being measured by the third means and wherein the microprocessor outputs the new closed sound wave signal $y_m(n)$ from the m-th number of the speakers, expressed as follows:

$$y_m(n) = \sum_{i=0}^{I-1} Wm(n, i) \times (n-i),$$

wherein (n−i) denotes the i-th number of the reference signal x(n), n denotes a sampling period, and i is an integer denoting a specific one of a number I of filter coefficients.

10. A system for reducing a sound in a limited space as set forth in claim 9, wherein, when determining that the identifying switch is turned off, the microprocessor compares the key code in the RAM with that in the ROM, the value stored in the RAM is used for the value of the clm(j) when the result of comparison indicates coincidence, and the standard value stored in the ROM is used for the value of Clm(j) when the result of comparison indicates no coincidence.

11. A system for reducing a sound in a limited space as set forth in claim 8, wherein said identification processing is such that a white noise is output from each of the speakers.

12. A system for reducing a sound in a limited space as set forth in claim 8, wherein said identification processing is such that an impulse sound wave is output from each of the speakers.

13. A system for reducing a vibration sound propagated into a vehicular compartment, comprising:

a) first means for receiving a harmonic sound signal of a vehicular engine vibration sound and outputting, against the harmonic signal, a cancelling sound having a magnitude substantially equal to a magnitude of the vibration sound and having a phase of 180-degrees relative to a phase of the vibration sound;

b) second means for detecting a residual vibration sound created by a combination of the vibration sound and the cancelling sound outputted by the first means;

c) third means for adaptively adjusting the cancelling sound from the first means on the basis of the residual vibration sound using a vibration propagation spatial acoustic transfer function from a position of the first means to that of the second means so as to reduce a vibration energy detected by the second means, thereby reducing total vibration propagated into the vehicular compartment;

d) a volatile memory for storing a measured newest vibration propagation spatial acoustic transfer function so as to update a previously measured vibration propagation spatial acoustic transfer function;

e) a non-volatile memory for storing a predetermined standard value of the vibration propagation spatial acoustic transfer function, and an identifying switch, wherein said third means includes a microprocessor, wherein said microprocessor determines whether the engine is stopped and determines whether the identifying switch is turned on or off upon determining that the engine has stopped, and, when determining that the identifying switch is turned on, said microprocessor compares an identification end code in the volatile memory with an identification end code in the non-volatile memory, determines that the measured value of the spatial acoustic transfer characteristic stored in the volatile memory is a correct value of the newest acoustic transfer characteristic derived upon a previous identification processing when the identification end codes coincide with each other, sets a key code indicating that the data in the volatile memory is correct, and executes the identification processing when the identification end codes do not coincide with each other until the identification end codes coincide with each other, and wherein said microprocessor of said third means adjusts the cancelling sound using the vibration

14. A system as set forth in claim 13, wherein:

said first means comprises M speakers, where M is an integer greater than 0 and said second means comprises L microphones, where L is an integer greater than 0;

said spatial acoustic transfer function represents an impulse response Clm from an mth speaker to an lth microphone where m and l are integers less than M and L, respectively; and said predetermined standard value of the vibration propagation spatial acoustic transfer function represents a response to white noise.

15. A system as set forth in claim 14, wherein said predetermined standard value of the vibration propagation spatial acoustic transfer function represents a response to a white noise generator applied during manufacturing shipment of the vehicle.

16. A system for reducing a sound in a limited space, comprising:

a) first means for receiving a sound wave generated due to a propagation from a noise source into the limited space, said noise source comprising a vehicular engine, and for transducing the sound wave to output an electrical signal according to the sound wave;

b) second means responsive to the electrical signal from said first means for calculating a new sound wave having the same amplitude as the sound wave and having a phase 180° opposite to the sound wave on a basis of an acoustic transfer characteristic of the limited space, said new sound wave interfering with said sound wave to reduce the total sound in the limited space;

c) third means for measuring the acoustic transfer characteristic of the limited space;

d) a volatile memory for storing the measured value of the acoustic transfer characteristic as its stored data;

e) a non-volatile memory for storing a standard value of the acoustic transfer characteristic as its stored data, said second means calculating the new sound wave on the basis of the standard value of the acoustic transfer characteristic derived from the non-volatile memory when the stored data in the volatile memory is erased, and f) fourth means, comprising an identifying switch for inputting a signal to said second means, wherein said second means includes a microprocessor, wherein said microprocessor determines whether the engine is stopped and determines whether the identifying switch is turned on or off upon determining that the engine has stopped, and, when determining that the identifying switch is turned on, said microprocessor compares an identification end code in the volatile memory with an identification end code in the non-volatile memory, determines that the measured value of the acoustic transfer characteristic stored in the volatile memory is a correct value of a newest acoustic transfer characteristic derived upon a previous identification processing when the identification end codes coincide with each other, sets a key code indicating that the data in the volatile memory is correct, and executes the identification processing when the identification end codes do not coincide with each other until the identification end codes coincide with each other, said microprocessor being further responsive to said signal from said fourth means by selecting one of said measured acoustic transfer characteristic from said volatile memory and said standard value of the acoustic transfer characteristic from said non-volatile memory for calculating the new sound wave.

17. A system as set forth in claim 16, wherein said identifying switch of said fourth means comprises a user operated switch means, said second means responding to indication of a first position of said user operated switch means by said signal from said fourth means by initiating a process to provide the measured value of the acoustic transfer characteristic to said volatile memory.

18. A system as set forth in claim 17, wherein said second means responding to indication of a second position of said user operated switch means by said signal from said fourth means by using said standard value of the acoustic transfer characteristic from said non-volatile memory for calculating the new sound wave.

* * * * *